United States Patent
Michos et al.

(10) Patent No.: US 11,000,711 B2
(45) Date of Patent: *May 11, 2021

(54) COMPOSITIONS FOR FORMING FILMS HAVING A DESIRED DEGREE OF OBSCURATION AND METHODS OF MAKING AND USING THE SAME

(75) Inventors: Demetrius Michos, Clarksville, MD (US); James Neil Pryor, West Friendship, MD (US)

(73) Assignee: W. R. Grace & Co.-Conn., Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/519,763

(22) PCT Filed: Dec. 14, 2010

(86) PCT No.: PCT/US2010/060202
§ 371 (c)(1),
(2), (4) Date: Jun. 28, 2012

(87) PCT Pub. No.: WO2011/081902
PCT Pub. Date: Jul. 7, 2011

(65) Prior Publication Data
US 2012/0288546 A1    Nov. 15, 2012

Related U.S. Application Data

(60) Provisional application No. 61/290,796, filed on Dec. 29, 2009.

(51) Int. Cl.
*A61Q 19/08* (2006.01)
*A61K 8/02* (2006.01)
*A61K 8/25* (2006.01)

(52) U.S. Cl.
CPC ............ *A61Q 19/08* (2013.01); *A61K 8/0279* (2013.01); *A61K 8/25* (2013.01); *A61K 2800/412* (2013.01)

(58) Field of Classification Search
CPC ........ A61Q 19/08; A61K 8/0279; A61K 8/25; A61K 2800/412; A61K 8/06
See application file for complete search history.

(56) References Cited

U.S. PATENT DOCUMENTS

| | | | |
|---|---|---|---|
| 2,786,042 A | 3/1957 | Iler | 260/37 |
| 2,801,185 A | 7/1957 | Iler | 106/288 |
| 3,657,680 A | 4/1972 | Stegina et al. | 337/308 |
| 3,924,032 A | 12/1975 | Hertl | 427/220 |
| 4,157,920 A | 6/1979 | Wason et al. | 106/292 |
| 4,764,424 A | 8/1988 | Ganga et al. | 428/327 |
| 4,851,214 A * | 7/1989 | Walters et al. | 424/65 |
| 4,877,595 A | 10/1989 | Klingle | |
| 4,948,578 A * | 8/1990 | Burger | A61K 8/0229 424/66 |
| 5,030,286 A | 7/1991 | Crawford et al. | 106/435 |
| 5,069,897 A * | 12/1991 | Orr | A61K 8/25 424/66 |
| 5,156,834 A * | 10/1992 | Beckmeyer | A61K 8/585 424/47 |
| 5,169,710 A * | 12/1992 | Qureshi | C08J 5/04 428/408 |
| 5,223,559 A | 6/1993 | Arraudeau et al. | |
| 5,558,071 A * | 9/1996 | Ward | F02P 3/02 123/598 |
| 5,704,362 A | 1/1998 | Hersh et al. | 128/680 |
| 5,830,485 A | 11/1998 | Gueret et al. | 424/401 |
| 5,917,069 A * | 6/1999 | Buckl | B01J 20/10 423/112 |
| 6,123,951 A | 9/2000 | Gueret et al. | 424/401 |
| 6,197,384 B1 | 3/2001 | Schubert et al. | 427/419 |
| 6,258,345 B1 | 7/2001 | Rouquet et al. | 424/64 |
| 6,333,043 B1 | 12/2001 | Gueret et al. | 424/401 |
| 6,333,053 B1 | 12/2001 | Simon | |
| 6,344,240 B1 | 2/2002 | Menon et al. | 427/220 |
| 6,380,265 B1 * | 4/2002 | Pryor | C01B 33/141 516/85 |
| 6,511,672 B2 | 1/2003 | Tan et al. | 424/401 |
| 6,579,851 B2 * | 6/2003 | Goeke | A61K 38/26 514/11.7 |
| 7,037,475 B2 | 5/2006 | Dokter et al. | 423/335 |
| 7,160,550 B2 * | 1/2007 | Brieva | A61K 8/25 424/401 |
| 7,245,434 B2 | 7/2007 | Nishida | |
| 7,531,184 B2 | 5/2009 | Horino et al. | 424/401 |
| 7,569,274 B2 | 8/2009 | Besse | |
| 8,172,938 B2 * | 5/2012 | Alright et al. | 106/672 |
| 8,461,129 B2 * | 6/2013 | Bolduc | A61L 15/28 127/49 |
| 2001/0032570 A1 | 10/2001 | Horino et al. | 106/486 |
| 2002/0141957 A1 | 10/2002 | Tan et al. | |

(Continued)

FOREIGN PATENT DOCUMENTS

| | | |
|---|---|---|
| CN | 1256118 A | 6/2000 |
| DE | 10349484 | 6/2005 |

(Continued)

OTHER PUBLICATIONS

Cab-O-Sil MSDS (Cabot Corp.), published May 24, 2006.*
Cab-O-Sil HS-5 product information (http://www.cabot-corp.com/Silicas-And-Aluminas/Products/PR200808140923AM3616/), accessed Jun. 11, 2013.*
"Aerosil 2008" (https://web.archive.org/web/20081119174046/http://www.aerosil.com/aerosil/en/industries/personalcare/antiperspirants) accessed Nov. 19, 2014.*

(Continued)

*Primary Examiner* — Andrew S Rosenthal

(57) ABSTRACT

Compositions suitable for use as cosmetic products (e.g., skin cream) are disclosed. Methods of making and using compositions suitable for use as cosmetic products are also disclosed.

20 Claims, 1 Drawing Sheet

(56) References Cited

U.S. PATENT DOCUMENTS

| | | | |
|---|---|---|---|
| 2003/0114572 A1 | 6/2003 | Travkina | |
| 2003/0131536 A1 | 7/2003 | Kostinko | |
| 2003/0206896 A1* | 11/2003 | O'Prey | A61K 8/345 424/94.63 |
| 2005/0031658 A1 | 2/2005 | Girier Dufournier et al. | |
| 2005/0058677 A1 | 3/2005 | Ricard et al. | 424/401 |
| 2005/0129638 A1 | 6/2005 | Dumousseaux | |
| 2005/0220729 A1 | 10/2005 | Luukas et al. | 424/59 |
| 2005/0220732 A1 | 10/2005 | Luukas et al. | 424/61 |
| 2005/0244364 A1 | 11/2005 | Luukas et al. | 424/78.3 |
| 2005/0260147 A1 | 11/2005 | Elliott et al. | |
| 2005/0271616 A1 | 12/2005 | Luukas et al. | 424/78.3 |
| 2005/0288410 A1 | 12/2005 | Farcet | 524/322 |
| 2006/0008431 A1 | 1/2006 | Farcet | 424/60 |
| 2006/0155052 A1 | 7/2006 | Schumacher et al. | |
| 2006/0193803 A1 | 8/2006 | Farcet | 424/70.1 |
| 2006/0194932 A1 | 8/2006 | Farcet | 525/477 |
| 2006/0210513 A1 | 9/2006 | Luizzi | |
| 2007/0183992 A1 | 8/2007 | Dumousseaux et al. | 424/59 |
| 2008/0031837 A1 | 2/2008 | Farcet et al. | 424/61 |
| 2008/0152680 A1 | 6/2008 | Brown et al. | 424/401 |
| 2008/0175804 A1 | 7/2008 | Farcet | 424/59 |
| 2008/0181859 A1 | 7/2008 | Farcet | 424/59 |
| 2008/0220026 A1 | 9/2008 | Maitra et al. | 424/400 |
| 2008/0248071 A1 | 10/2008 | Doat et al. | |
| 2009/0047308 A1 | 2/2009 | Farcet | 424/401 |
| 2009/0054534 A1 | 2/2009 | Kitamura | 514/769 |
| 2009/0060849 A1 | 3/2009 | Song et al. | 424/49 |
| 2009/0081261 A1 | 3/2009 | Thevenet | 424/401 |
| 2009/0082460 A1 | 3/2009 | Pavlin | 514/617 |
| 2009/0087463 A1 | 4/2009 | Yagyu et al. | 424/401 |
| 2009/0117160 A1 | 5/2009 | Dumousseaux et al. | 424/401 |
| 2009/0117162 A1 | 5/2009 | Victor et al. | 424/401 |
| 2009/0123402 A1 | 5/2009 | Oi | 424/64 |
| 2009/0126316 A1 | 5/2009 | Ilekti et al. | 53/111 |
| 2009/0130037 A1 | 5/2009 | Thevenet et al. | 424/61 |
| 2009/0142382 A1 | 6/2009 | Shah et al. | 424/401 |
| 2009/0148393 A1 | 6/2009 | Maitra et al. | 424/63 |
| 2009/0155373 A1 | 6/2009 | Huang et al. | 424/499 |
| 2009/0155586 A1 | 6/2009 | Maitra et al. | 428/338 |
| 2009/0175619 A1 | 7/2009 | Maitra et al. | |
| 2009/0311159 A1 | 12/2009 | Gray | 423/335 |
| 2010/0247914 A1 | 9/2010 | Enomoto et al. | 428/402 |
| 2010/0266649 A1 | 10/2010 | Maitre et al. | 424/401 |
| 2011/0028412 A1* | 2/2011 | Cappello | A61K 31/7004 514/25 |
| 2013/0041004 A1* | 2/2013 | Drager | A61K 9/08 514/394 |
| 2013/0084243 A1* | 4/2013 | Goetsch | C07K 16/2863 424/1.49 |
| 2013/0096073 A1* | 4/2013 | Sidelman | A61K 38/1709 514/21.6 |
| 2013/0309497 A1* | 11/2013 | Takezaki | C08J 3/14 428/402 |

FOREIGN PATENT DOCUMENTS

| | | | |
|---|---|---|---|
| EP | 0658523 | 6/1995 | C23D 5/04 |
| EP | 709083 A2 * | 5/1996 | |
| EP | 0709083 A2 * | 5/1996 | A61K 8/25 |
| EP | 1 999 335 | 4/2002 | |
| EP | 1 582 194 | 7/2010 | |
| JP | 08-59436 | 8/1994 | |
| JP | 2007-316488 | 12/1995 | |
| JP | 2001-199839 | 7/2001 | |
| JP | 2002-20235 | 1/2002 | A61K 7/02 |
| JP | 2002173415 | 6/2002 | |
| JP | 2004352606 | 12/2004 | |
| WO | 2003015727 | 2/2003 | |
| WO | 2003054089 | 7/2003 | |
| WO | 2004073689 | 9/2004 | |
| WO | 2005082320 | 9/2005 | |
| WO | 2005115313 | 1/2008 | |
| WO | 2008/022836 | 2/2008 | C01B 33/18 |
| WO | WO-2008022836 A1 * | 2/2008 | C09C 1/30 |
| WO | WO 2008022836 A1 * | 2/2008 | C01B 33/183 |
| WO | 2008079560 | 7/2008 | |
| WO | 20090885484 | 7/2009 | |
| WO | 20090892565 | 7/2009 | |
| WO | 2013/029125 | 3/2013 | A61Q 1/04 |

OTHER PUBLICATIONS

"Aerosil R805" (https://www.aerosil.com/www2/uploads/productfinder/AEROSIL-R-805_1836_12112010153430.pdf) Sep. 2014.*

Inoxia (http://www.inoxia.co.uk/products/chemicals/inorganic-compounds/cab-o-sil) accessed Jul. 15, 2015, pp. 1-3.*

Dow Corning ST-Cyclomethicone 5-NF product information (http://www4.dowcorning.com/DataFiles/090007c88020e2df.pdf), published May 21, 2009.*

Silicones Plus (http://static1.1.sqspcdn.com/static/f/356390/22166534/1363122117343/Silicones+Plus+Brochure_1.pdf?token=%2Be%2BXKBC9OnwaK3fthVDMKTVrgHM%3D) accessed Jul. 15, 2015, pp. 1-2.*

Cabot "Cab-O-Sil M5P" (www.sanmargroup.com/images/Cabot_Brochure.pdf) accessed Aug. 3, 2016, pp. 1-4.*

Hind Exports (http://www.hindexports.com/bentonite_power.html) 2012, p. 1-2.*

Polymer Database (http://polymerdatabase.com/polymers/nylon12.html) 2015, pp. 1-2 (Year: 2015).*

Chemical Book (http://www.chemicalbook.com/ChemicalProductProperty_US_CB4292618.aspx) accessed Nov. 14, 2017, pp. 1-2 (Year: 2017).*

Index of Refraction (http://hyperphysics.phy-astr.gsu.edu/hbase/Tables/indrf.html) accessed Nov. 14, 2017, p. 1-2 (Year: 2017).*

Hodgson A.S.—Bailey's Industrial oil and fat products, ed. 5, vol. 4; Refining and bleaching, p. 157-212—1996, Wiley-Interscience Publication—XP002470798 ISBN: 0-471-59428-8.

Quantification of the Soft Focus Effect, Cosmetics & Toilestries, (Ralf Emmert), vol. 111, pp. 57-61 (1996).

Cosmetics & Toiletries—Quantification of the Soft-Focus Effect Measuring Light-Diffusing Characteristics of Cosmetic Pigments and Powders—Jul. 1996 By: Dr. Ralf Emmert, PhD, Rona/EM industries, Hawthorne, NY, USA.

Intellectual Property Trends in Color Cosmetics Robert Y. Lochhead and Laura Anderson—The Institute for Formulation Science and the School of Polymers & High Performance Materials—The University of Southern Mississippi.

U.S. Appl. No. 61/290,796, filed Dec. 29, 2009.

Wason, J.Soc.Cosmet. Chem., 1978, 29, pp. 497-521.

Chiao et al., Analytical Chem., 1957 vol. 29 (11), pp. 1678-1681.

Cab-o-silHS-5 Technical Datasheet, obtained online at: http://adhesives.specialchem.com/product/a-cabot-cab-o-sil-hs-5, Jul. 2, 2015, 1 page.

Sun et al., J.Cosmet., Sci. 2005,vol. 56, pp. 253-265.

Aerosil Colloidal Silicon Dioxide for Pharmaceuticals, degussa, creatng essentials, No. 1281, Apr. 2006, pp. 1-24.

Cleaning Technology, CPCH1261847P, pp. 1-3.

Shrivastava, et al., "Design, Optimization, Preparation and Evaluation of Dispersion Granulae of Valsartan and Formulation into Tablets", Current Drug Delivery, vol. 6, No. 1, 2009, pp. 1-10.

Khetarpal, et al, Formulation Development of Stable Solid Oral Dosage Form of Valproic Acid Using Colloidal Silica:, Intl. Jrnl Drug Delivery 4 (2), 2012, pp. 266-274.

"Marzipan Souffle:make up base, Sebum Control", Dow Corning, Formulation Information New Skin Care Application.

"Pharm Silica Insights", Evonik Industries, Issue 1, 2012, pp. 1-6.

* cited by examiner

COMPOSITIONS FOR FORMING FILMS HAVING A DESIRED DEGREE OF OBSCURATION AND METHODS OF MAKING AND USING THE SAME

FIELD OF THE INVENTION

The present invention is directed to compositions suitable for use as cosmetic products (e.g., skin creams). The present invention is further directed to methods of making and using compositions suitable for use as cosmetic products.

BACKGROUND OF THE INVENTION

Cosmetic creams having the ability to hide wrinkles and other skin imperfections are widely used. Some creams accomplish this task by physical filling of the skin depression, giving the appearance of smooth skin. Another way to hide wrinkles and other skin imperfections is to create a film on the skin surface, which is capable of obscuring the imperfection via light diffusion. According to this method, particles present in the film scatter light producing a diffuse appearance of the underlying skin. Due to this diffuse appearance, the perception of smooth skin is created, and the unwanted skin imperfections are being obscured.

The use of light diffusing pigments for cosmetic applications has been described in *Quantification of the Soft Focus Effect, Cosmetics & Toiletries*, (Ralf Emmert), vol. 111, pp. 57-61 (1996) (hereinafter, "the Emmert article"). In the Emmert article, the use of silica in light diffusing cosmetics is discouraged due to the similarity of the refractive index of silica (RI=1.46) with that of cosmetic oils (RI=1.45-1.60). Consistent with the Emmett article was the conventional thinking that large differences in refractive index between vehicle and particle were necessary to produce a desired optical effect (i.e., maximum light scattering).

In addition, conventional thinking regarding the use of light diffusing pigments has been to load a composition with light diffusing pigments so as to maximize intra-film light scattering. FIG. 1 illustrates this principle. As shown in FIG. 1, exemplary film 10 comprises a vehicle matrix 11 with light diffusing pigments/particles 12 dispersed therein. When light 13 enters film 10 through upper surface 14, light diffusing pigments/particles scatter light 13 as shown by arrows 15. Given the surface smoothness of upper surface 14 very little light scattering takes place at upper surface 14 relative to an amount of intra-film light scattering that takes place within exemplary film 10.

Efforts continue to develop new approaches for hiding wrinkles and other skin imperfections. Efforts continue to develop obscuring compositions that are easily formulated so as to produce films and coatings that possess desired obscuration properties that are independent of film or coating thickness.

SUMMARY OF THE INVENTION

The present invention relates to the discovery of compositions suitable for use as a cosmetic product that has the ability to hide wrinkles and other skin imperfections. The compositions may be utilized in a variety of applications, but are particularly useful as a cosmetic product (i.e., a composition applied onto cutaneous and keratinous substrates) capable of hiding wrinkles and other imperfections.

The disclosed compositions comprise particulate material (e.g., silica particles) within a fluid phase that comprises at least one non-volatile component and at least one volatile component. When applied onto a cutaneous or keratinous substrate (e.g., facial skin), the disclosed compositions desirably form a continuous, transparent film that is capable of obscuring wrinkles and other imperfections in the substrate while allowing the natural tone of the substrate (e.g., a natural skin tone) to be visible through the film. Further, by having a rough outermost surface, the continuous, transparent film enables light scattering at the film surfaces, and does not rely on light scattering within the film.

It has been discovered that the use of particulate material having a Total Available Fluid Absorption Capacity of Particulate (TAFACP) value of greater than zero; and a fluid phase comprising a non-volatile component, and a volatile component; wherein the non-volatile component is present in the composition in an amount of at least that which fills the pores of the particulate material and inter particle voids produces compositions that possess superior obscuration properties, as well as a desired degree of outermost surface roughness and transparency when applied as a film onto a substrate (e.g., skin).

It has further been discovered that the use of particulate material having a Total Available Fluid Absorption Capacity of Particulate (TAFACP) value of greater than zero in combination with a fluid phase comprising a non-volatile component and a volatile component, wherein the composition has a weight ratio, R, of total non-volatile content (NVC) to TAFACP with R ranging from greater than 0 to less than about 8.0 produces compositions that possess superior obscuration properties, as well as a desired degree of outermost surface roughness and transparency when applied as a film onto a substrate (e.g., skin). By utilizing a desired range of non-volatile (NVC) content and particulate concentration (for a given particulate), optimized obscuration results may be obtained.

It has been further discovered that compositions containing an insufficient amount of non-volatile content (NVC) result in an objectionably opaque appearance when applied onto a treated skin area in the form of a film or coating. In addition, compositions containing an excessive amount of non-volatile (NVC) result in a glossy appearance when applied onto a treated skin area in the form of a film or coating, which is also undesirable as a cosmetic product.

Although a variety of particulate material may be used to form the obscuring compositions and films of the present invention, it has been discovered that, in some embodiment, the use of particles that have a refractive index similar to that of the non-volatile component present in the composition/film results in enhanced obscuration properties in the resulting film. In these embodiments, the particles within the film are substantially ineffective as light scatterers; however, when incorporated into a film with an appropriate amount of the non-volatile(s), the resulting film has desired obscuration properties due to scattering of transmitted light as the result of the uneven (i.e., rough) outermost surface of the film. By restricting light scattering to the outermost surface of the film, the obscuring properties of the film are independent of film thickness. Consequently, a film applied over skin desirably provides a very uniform appearance, both in obscuration and reflectance, to the skin even if the film thickness is not particularly uniform.

Another benefit resulting from light scattering at the outermost surface of a film versus light scattering within the film is the fact that the obscuration property of a rough film is less dependent on the particle concentration in the film composition when compared to films in which intra-film light scattering is the dominant mechanism. Consequently, the present invention allows a composition/film formulator greater freedom (1) to vary the amount of particulate material within a given composition, as well as (2) to incorporate other ingredients (e.g., emollients, fragrances, soluble polymers, etc.) into the given composition.

In one exemplary embodiment, the composition of the present invention comprises particulate material having a Total Available Fluid Absorption Capacity of Particulate (TAFACP) value of greater than zero; and a fluid phase comprising a non-volatile component, and a volatile component; wherein the composition has a weight ratio, R, of total non-volatile content (NVC) to TAFACP, and R ranges from greater than 0 to less than about 8.0. Compositions of the present invention may further comprise one or more additional components including, but not limited to, deionized water, a humectant, an emollient, a fragrance, soluble polymers, or any combination thereof.

In another exemplary embodiment, the composition of the present invention comprises particulate material having a Total Available Fluid Absorption Capacity of Particulate (TAFACP) value of greater than zero; and a fluid phase comprising a non-volatile component, and a volatile component; wherein the particulate material and the non-volatile component possess a substantially similar refractive index.

The present invention is also directed to methods of making compositions capable of obscuring surface imperfections. In one exemplary embodiment, the method of making a composition comprises forming a mixture comprising particulate material having a Total Available Fluid Absorption Capacity of Particulate (TAFACP) value of greater than zero; and a fluid phase comprising a non-volatile component, and a volatile component; wherein the composition has a weight ratio, R, of total non-volatile content (NVC) to TAFACP, and R ranges from greater than 0 to less than about 8.0. The method of making a composition may further comprise incorporating one or more additional components into the mixture, wherein the one or more additional components include, but are not limited to, deionized water, a humectant, an emollient, a fragrance, soluble polymers, or any combination thereof.

In another exemplary embodiment, the method of making a composition comprises choosing a value of R, wherein R represents a weight ratio of total non-volatile content (NVC) to a Total Available Fluid Absorption Capacity of Particulate (TAFACP) value of a particulate material; and forming a mixture of (i) the particulate material and (ii) a fluid phase comprising a non-volatile component, and a volatile component so that a resulting R value of the mixture equals the chosen value of R. In some desired embodiments, the method of making a composition comprises choosing a value of R ranging from greater than 0 to less than about 8.0. The method of making a composition may further comprise incorporating one or more additional components into the mixture, wherein the one or more additional components include, but are not limited to, deionized water, a humectant, an emollient, a fragrance, soluble polymers, or any combination thereof, and incorporation of the one or more additional components does not negatively impact the resulting chosen R value.

The present invention is also directed to films for obscuration. In one exemplary embodiment, the present invention comprises particulate material having a Total Available Fluid Absorption Capacity of Particulate (TAFACP) value of greater than zero; and a fluid phase comprising a non-volatile component and a volatile component; the film (i) having a weight ratio, R, of total non-volatile content (NVC) to TAFACP with R ranging from greater than 0 to less than about 8.0, and (ii) comprising a substantially transparent continuous film having an outermost rough surface, the outermost rough surface comprising one or more lower surface points along the outermost rough surface and one or more upper surface points along the outermost rough surface, the one or more lower surface points being separated from the one or more upper surface points in a z direction by a distance of from about 0.05 to about 20.0 µm.

In a further exemplary embodiment, the present invention relates to a transparent coating comprising particulate material having a Total Available Fluid Absorption Capacity of Particulate (TAFACP) value of greater than zero; and a fluid phase comprising a non-volatile component, and a volatile component; wherein total transmission and diffuse transmission of light through the transparent coating remains substantially constant as thickness of the coating increases.

In another exemplary embodiment, the present invention relates to a transparent coating for hiding skin imperfections comprising particulate material having a Total Available Fluid Absorption Capacity of Particulate (TAFACP) value of greater than zero; and a fluid phase comprising a non-volatile component, and a volatile component; wherein the particulate material does not provide measurable intra-film light scattering in the coating but provides surface scattering, which hides cutaneous and keratinous imperfections.

The present invention is further directed to methods of using the compositions of the present invention. In one exemplary embodiment, the method of using the composition of the present invention comprises a method of forming a coating on a substrate, wherein the method comprises coating at least a portion of the substrate with a composition comprising particulate material having a Total Available Fluid Absorption Capacity of Particulate (TAFACP) value of greater than zero; and a fluid phase comprising a non-volatile component, and a volatile component; wherein the composition has a weight ratio, R, of total non-volatile content (NVC) to TAFACP, and R ranges from greater than 0 to less than about 8.0. The substrate may comprise a variety of substrates including cutaneous and keratinous substrates, such as skin, hair, nails, etc.

Other exemplary methods of using the compositions of the present invention comprise a method of hiding skin imperfections, wherein the method comprises applying a composition onto an outer skin surface, wherein the composition comprises (i) particulate material having a Total Available Fluid Absorption Capacity of Particulate (TAFACP) value of greater than zero, and (ii) a fluid phase comprising a non-volatile component and a volatile component; wherein the composition (i) has a weight ratio, R, of total non-volatile content (NVC) to TAFACP with R ranging from greater than 0 to less than about 8.0, and (ii) forms a substantially transparent continuous film having an outermost rough surface, the outermost rough surface comprising one or more lower surface points along the outermost rough surface and one or more upper surface points along the outermost rough surface, the one or more lower surface points being separated from the one or more upper surface points in a z direction by a distance of from about 0.05 to about 20.0 µm.

The present invention is further directed to multi-layer articles comprising a substrate and the composition of the present invention on an outer surface of the substrate. In one exemplary embodiment, the multi-layer article comprises skin having an outer skin surface; and the herein disclosed obscuring composition on the outer skin surface.

These and other features and advantages of the present invention will become apparent after a review of the following detailed description of the disclosed embodiments and the appended claims.

DETAILED DESCRIPTION OF THE INVENTION

Figure 1:
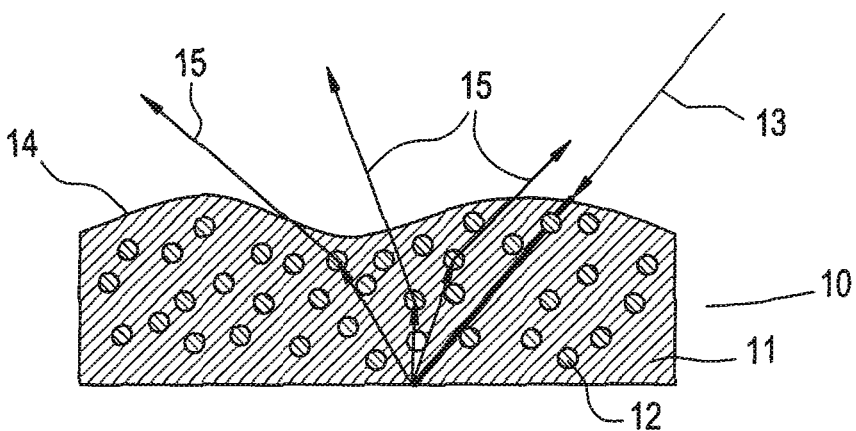
FIG. 1 depicts an exemplary conventional light diffusing pigment/particle loaded film so as to maximize intra-film light scattering.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise. Thus, for example, reference to "an oxide" includes a plurality of such oxides and reference to "oxide" includes reference to one or more oxides and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

The term "particles" refers to porous or nonporous particles formed via any known process including, but not limited to, a solution polymerization process such as for forming colloidal particles, a continuous flame hydrolysis technique such as for forming fused particles, a gel technique such as for forming gelled particles, and a precipitation technique such as for forming precipitated particles. The particles may be composed of organic and/or inorganic materials and combinations thereof. In one exemplary embodiment the particles are composed of inorganic materials such as metal oxides, sulfides, hydroxides, carbonates, nitrides, phosphates, etc, but are preferably metal oxides. The particles may be a variety of different symmetrical, asymmetrical or irregular shapes, including chain, rod or lath shape. The particles may have different structures including amorphous or crystalline, etc. The particles may include mixtures of particles comprising different compositions, sizes, shapes or physical structures, or that may be the same except for different surface treatments.

As used herein, "metal oxides" is defined as binary oxygen compounds where the metal is the cation and the oxide is the anion. The metals may also include metalloids. Metals include those elements on the left of the diagonal line drawn from boron to polonium on the periodic table. Metalloids or semi-metals include those elements that are on the right of this line. Examples of metal oxides include silica, alumina, titania, zirconia, silicates, aluminosilicates, etc., and mixtures thereof.

As used herein, "organic" materials include those compounds or materials that include carbon content, which may be natural or synthetic. These materials may be natural and/or synthetic polymers that may be homopolymers or copolymers and include, but are not limited to, biopolymers, fluoropolymers, polyterpenes, phenolic resins, polyanhydrides, polyesters, polyolefins, rubbers, silicones, superabsorbent polymers, vinyl polymers, and combinations thereof. Examples of organic materials include, but are not limited to, polypropylenes, polyethylenes, polyamides, polytetrafluoroethylenes, polymethylmethacrylates, silicones, etc., and mixtures thereof.

As used herein the term "porous" particles having significant internal porosity as measured by nitrogen porisimetry, i.e., a porosity of more than about 0.05 cc/g, and the term "non-porous" means particles having little or no internal porosity, i.e., an internal porosity of less than about 0.05 cc/g. Examples of porous particles include, silica gel, precipitated silica, filmed silica, boehmite alumina, etc., and examples of non-porous particles include colloidal silica, alumina, titania, etc.

As used herein, the term "substantially" means within a reasonable amount, but includes amounts which vary from about 0% to about 50% of the absolute value, from about 0% to about 40%, from about 0% to about 30%, from about 0% to about 20% or from about 0% to about 10%.

As used herein, the term "fluid" means a gas, liquid, and supercritical fluid, including fluids that are volatile and non-volatile, and are natural and synthetic. Examples include, but are not limited to, oils, solvents, water, polymers, waxes, glycerin, other liquids, and mixtures thereof.

As used herein, the term "light scattering" or other electromagnetic radiation is the deflection of rays in random directions by irregularities in the propagation medium, or in a surface or interface between two media. Scattering from a surface or interface can also be called diffuse reflection.

In one exemplary embodiment, the composition of the present invention comprises particulate material having a Total Available Fluid Absorption Capacity of Particulate (TAFACP) value of greater than zero; and a fluid phase comprising a non-volatile component, and a volatile component; wherein the non-volatile component is present in the composition in an amount of at least that which fills the pores of the particulate material and inter particle voids. In embodiments where the particulate material is not porous, then the amount of non-volatile component present in the formulation includes that which is necessary to fill only the inter particle voids. Accordingly, depending on the porosity of the particulate material, the amount of non-volatile component in the formulation may vary considerably.

The present invention is directed to compositions comprising (i) particulate material having a Total Available Fluid Absorption Capacity of Particulate (TAFACP) value of greater than zero, and (ii) a fluid phase comprising a non-volatile component and a volatile component. The compositions have a weight ratio, R, of total non-volatile content (NYC) to TAFACP that desirably ranges from greater than 0 to less than about 8.0. The present invention is further directed to methods of making compositions comprising (i) particulate material having a Total Available Fluid Absorption Capacity of Particulate (TAFACP) value of greater than zero, and (ii) a fluid phase comprising a non-volatile component and a volatile component, wherein the resulting composition has a weight ratio, R, of total non-volatile content (NVC) to TAFACP that desirably ranges from greater than 0 to less than about 8.0. The present invention is even further directed to methods of forming a coating or film on a substrate, wherein the coating or film comprises (i) particulate material having a Total Available Fluid Absorption Capacity of Particulate (TAFACP) value of greater than zero, and (ii) a fluid phase comprising a non-volatile component and a volatile component. The present invention is even further directed to coatings or film, coated substrates, and multi-layer articles comprising the disclosed composition on a substrate such as skin.

The compositions of the present invention provide one or more benefits and/or technical advantages that were not previously addressed in the art of compositions and coatings formed therefrom. For example, the disclosed compositions and resulting coatings utilize (i) particulate material having a Total Available Fluid Absorption Capacity of Particulate (TAFACP) value of greater than zero, and (ii) a fluid phase comprising a non-volatile component and a volatile component in amounts that enable the formation of coatings and films having (1) a desired degree of outer surface roughness, which results in a predominance of surface light scattering, (2) a desired degree of transparency, and (3) a desired degree of obscuration properties.

A description of exemplary compositions and composition components is provided below.

I. Compositions

The compositions of the present invention may comprise a number of individual components. A description of individual components and combinations of individual components is provided below. Further, the compositions of the present invention may be presented in various forms. A description of types of compositions is also provided below.

A. Composition Components

The compositions of the present invention may comprise one or more of the following components.

1. Particulate Material

The compositions of the present invention comprise particulate material having a Total Available Fluid Absorption Capacity of Particulate (TAFACP) value of greater than zero. Suitable particulate materials having a TAFACP value of greater than zero include, but are not limited to, alumina, boron nitride, nylon, silica, silica/titania composites, and any combination thereof. For example, the particulate material may be porous or non-porous and may be in the form of a powder or slurry including aqueous and non-aqueous fluids. TAFACP is measured by multiplying the oil adsorption of the particulate material by the weight of the particulate material in the formulation.

Suitable particulate materials for use in the present invention have TAFACP values greater than zero that depend on, for example, the particle composition and the degree of particle porosity and amount present in the formulation.

In one embodiment, the metal oxide particulate comprises porous materials, such as precipitated metal oxide (e.g., silica, alumina, etc.) or metal oxide gel. As it is well known in the art, the formation of precipitated silica occurs in a reaction between waterglass and an acid via first forming a seed of primary particles which can be grown to larger particles, followed by an aggregation and then by an agglomeration of these aggregates. Depending on the reaction conditions, the agglomerates can be grown even more together by a so called reinforcement. At a certain agglomerate size and concentration, the hydrous silica begins to settle from the reaction slurry as a precipitate. To isolate the hydrous silica from the slurry and to remove the reaction electrolyte from the crude silica, the precipitate is filtered from the slurry and washed. The resulting filtercake then is dried using drying equipment as known in the art. Depending on the method and extend of drying, a stiffening of the silica structure will occur during the drying step in which irreversible Si—O—Si-links are formed from initial silanol groups. Processes for making precipitated metal oxides include those set forth in U.S. Pat. Nos. 7,037,475B1; 5,030,286 and 4,157,920, the entire subject matter of which is incorporated herein by reference. In a further embodiment of the present invention, the colloidal metal oxide particles stem from the primary particles, grown particles, aggregated particles, agglomerated particles or the filtercake of a general metal oxide precipitation process as described above.

Methods of preparing inorganic oxide gels are well known in the art and include those set forth in U.S. Pat. No. 6,380,265, the entire subject matter of which is incorporated herein by reference. For example, a silica gel is prepared by mixing an aqueous solution of an alkali metal silicate (e.g., sodium silicate) with a strong acid such as nitric or sulfuric acid, the mixing being done under suitable conditions of agitation to form a clear silica sol which sets into a hydrogel, i.e., macrogel, in less than about one-half hour. The resulting gel is then washed. The concentration of inorganic oxide, i.e., $SiO_2$, formed in the hydrogel is usually in the range of about 10 and about 50 weight percent, with the pH of that gel being from about 1 to about 9, preferably 1 to about 4. A wide range of mixing temperatures can be employed, this range being typically from about 20 to about 50° C. The newly formed hydrogels are washed simply by immersion in a continuously moving stream of water which leaches out the undesirable salts, leaving about 99.5 weight percent or more pure inorganic oxide behind. The pH, temperature, and duration of the wash water will influence the physical properties of the silica, such as surface area (SA) and pore volume (PV). Silica gel washed at 65-90° C. at pH's of 8-9 for 15-36 hours will usually have SA's of 250-400 and form aerogels with PV's of 1.4 to 1.7 cc/gm. Silica gel washed at pH's of 3-5 at 50-65° C. for 15-25 hours will have SA's of 700-850 and form aerogels with PV's of 0.6-1.3. These measurements are generated by $N_2$ porosity analysis. Methods for preparing inorganic oxide gels such as alumina and mixed inorganic oxide gels such as silica/alumina cogels are also well known in the art. Methods for preparing such gels are disclosed in U.S. Pat. No. 4,226,743, the contents of which are incorporated by reference. In general, alumina gels are prepared by mixing alkali metal aluminates and aluminum sulfate. Cogels are prepared by cogelling two metal oxides so that the gels are composited together. For example, silica alumina cogels can be prepared by gelling an alkali metal silicate with an acid or acid salt, and then adding alkali metal aluminate, aging the mixture and subsequently adding aluminum sulfate. The gel is then washed using conventional techniques.

Porous particulate materials of the present invention may have a pore volume that makes the particles desirable formulation components. Typically, the porous particles have a pore volume as measured by nitrogen porosimetry of at least about 0.20 cc/g, and more typically, 0.30 cc/g. In one exemplary embodiment of the present invention, the porous particles have a pore volume as measured by nitrogen porosimetry of at least about 0.30 cc/g. Desirably, the porous particles have a pore volume as measured by nitrogen porosimetry of from about 0.30 to about 0.85 cc/g.

Porous particulate materials of the present invention also have a surface area as measured by the BET method (i.e., the Brunauer Emmet Teller method) of at least about 1 $m^2/g$. In one exemplary embodiment of the present invention, the porous particles have a BET surface area of from about 1 $m^2/g$ to about 1000 $m^2/g$. In a further exemplary embodiment of the present invention, the porous particles have a BET surface area of at least about 10 $m^2/g$.

Pore volume and surface area may be measured using, for example, an Autosorb 6-B unit commercially available from Quantachrome Instruments (Boynton Beach, Fla.). Typically, the pore volume and surface area of porous powder is measured after drying at about 150° C., and degassing for about 3 hours at 400° C. under vacuum (e.g., 50 millitorr).

The particulate materials typically have an average particle size ranging from about 0.1 to about 35 microns (μm). As used herein, the term "average particle size" refers to the average of the largest dimension of each particle within a set of particles. In some exemplary embodiments, the particulate materials have an average particle size ranging from about 1 to about 20 μm. In more desired embodiments, the particulate materials have an average particle size ranging from about 2 to about 10 μm (e.g., equal to or less than about 10, 9, 8, 7, 6, 5, 4, 3, 2, 1 microns and any size below one micron including 900, 800, 700, 600, 500, 400, 300, 200, or 100 nanometers, and even less than about 100 nanometers).

The particulate materials are typically present in the compositions of the present invention in an amount greater than 0 weight percent (wt %) and up to about 80 wt % based on a total weight of the composition. In some exemplary embodiments, the compositions comprise one or more particulate materials in an amount ranging from about 1 wt % to about 50 wt %, more typically, from about 1 wt % to about 20 wt %, and even more typically, from about 1 wt % to about 10 wt %, based on a total weight of the composition. For some exemplary embodiments of cream formulations, the amount of particulate materials typically present in the formulation may be greater than 0 wt % up to about 20 wt %, more typically, from about 1 wt % to about 10 wt %, and even more typically, from about 2 wt % to about 8 wt %, based on the total weight of composition.

In some exemplary embodiments, it may be beneficial to choose particulate material(s) having a refractive index (RI) that either matches or is relatively close to the refractive index of one or more components used in the fluid phase (discussed below). Typically, the particulate material(s) have a refractive index (RI) ranging from about 1.2 to about 1.8. In some exemplary embodiments, the particulate material comprises silica particles having a refractive index of about 1.4 to about 1.6.

In an exemplary embodiment, the particulate materials may be surface treated to change the surface properties of the materials. For example, the surface of the particulate materials may be treated to render them hydrophobic, such as by treatment with various organic materials (e.g., silanes, siloxanes, etc.). Since the surfaces of certain metal oxides are very hydrophilic (e.g., silica), the particulates tend to aggregate or agglomerate into larger particulates. If the surface of the metal oxide particulates is treated with hydrophobic material, the particulates do not aggregate, thereby remaining discrete and stable particles. Such hydrophobic materials include a variety of organic compounds, such as silanes, esters, alcohols, etc., and examples for rendering hydrophilic metal oxides hydrophobic may be found in U.S. Pat. Nos. 2,786,042 and 2,801,185, the entire subject matter of which is incorporated herein by reference. U.S. Pat. Nos. 6,344,240; 6,197,384; 3,924,032; and 3,657,680; and EP 0658523, describe various particulate surface treatments that may be utilized in this embodiment of the present invention, the entire subject matter of which is incorporated herein by reference.

In another exemplary embodiment, the particulate material may include a combination of various types of particulate material, such as particles of different size, shape, porosity, composition, refractive index, etc.

2. Fluid Phase Materials

The compositions of the present invention also comprise a fluid phase comprising a non-volatile component and a volatile component. The fluid phase may comprise a single fluid product having both a non-volatile component and a volatile component that are miscible with each other or two or more fluid products that, in combination, contribute to the non-volatile component and the volatile component (i.e., separate phases).

The fluid phase is typically present in the compositions of the present invention in an amount greater than 0 wt % and up to about 99.0 wt % based on a total weight of the composition. In some exemplary embodiments, the compositions comprise a fluid phase in an amount ranging from about 10.0 wt % to about 98.0 wt %, more typically, from about 25.0 wt % to about 80.0 wt %, and even more typically, from about 35.0 wt % to about 65.0 wt %, based on a total weight of the composition.

The amount of the non-volatile component in a given composition is sufficient to provide a resulting composition having a weight ratio, R, of total non-volatile content (NVC) to TAFACP that desirably ranges from greater than 0 to less than about 8.0. In some exemplary embodiments, R ranges from about 0.5 to about 7.4. In other exemplary embodiments, R ranges from about 3.0 to about 6.0. It should be understood that, depending on the chosen components for a given composition, R may be any value between about 0.5 to about 7.4 (e.g., 0.5, 0.6, 0.7 . . . 7.1, 7.2, 7.3 and 7.4) as long as the resulting composition, when applied onto a substrate as a film/coating (e.g., on to skin), produces a film having a rough upper surface, a desired degree of transparency and a desired degree of obscuration properties.

Typically, the non-volatile component and the volatile component may be present in any amount relative to one another as long as a desired value for R results from the combination. In some exemplary embodiments, the fluid phase comprises from about 1.0 to about 60.0 wt % of the non-volatile component, and from about 99.0 to about 40.0 wt % of the volatile component, based on a total weight of the fluid phase. In further exemplary embodiments, the fluid phase comprises from about 1.0 to about 40.0 wt % of the non-volatile component, and from about 99.0 to about 60.0 wt % of the volatile component, based on a total weight of the fluid phase. In other exemplary embodiments, the fluid phase comprises from about 1.6 to about 16.0 wt % of the non-volatile component, and from about 98.4 to about 84.0 wt % of the volatile component, based on a total weight of the fluid phase.

In some exemplary embodiments, it may be beneficial to choose one or more fluids having a refractive index (RI) that either matches or is relatively close to the refractive index of one or more particulate material. Typically, suitable fluids have a refractive index (RI) ranging from about 1.2 to about 1.8. In some exemplary embodiments, the one or more fluids have a refractive index of about 1.4 to about 1.6.

Suitable non-volatile components include, but are not limited to, oils, such as olive oils, sunflower oils, and the like; waxes, such as polyethylene waxes, and the like; glycerin; soluble polymers; and mixtures thereof. A number of commercially available products contributing to the non-volatile components may be used in the present invention, including, but are not limited to, fluids commercially available under the trade designation DOW CORNING® 1501, DOW CORNING® 5329 and DOW CORNING® 5200, all of which are commercially available from Dow Corning, Corporation (Midland, Mich.); Crodamol CP, Crodamol DIBA, Crodamol MM, Crodamol GTCC, Crodamol ICS, all of which are available from Croda Inc.; Cetiol J-600, Cetiol A, Cetiol 868, Cetiol CC, Cetiol LDO, all of which are available from Cognis Corporation.

Suitable volatile components include, but are not limited to, volatile silicones, such as DOW CORNING® 245 Fluid; water; solvents, such as ethanol; volatile fragrances; and the like; and mixtures thereof.

3. Additional Ingredients

The compositions of the present invention may further comprise one or more additional components. Suitable additional components for use in the compositions of the present invention include, but are not limited to, deionized (DI) water, humectants, surfactants, emollients, fragrances, polymers (including insoluble polymers which may form secondary particles, or soluble polymers) or any combination thereof.

Typically, the compositions of the present invention comprise deionized (DI) water. When present, the deionized (DI) water is present in an amount ranging from about 50 to about 90 wt % based on a total weight of a given composition. In some exemplary embodiments, deionized (DI) water is present in a given composition in an amount ranging from about 60 wt % to about 80 wt %, more typically, from about 70 wt % to about 76 wt %, and even more typically, from about 72 wt % to about 74 wt %, based on a total weight of the composition. However, the amount of deionized (DI) water, when present, may vary as desired.

Each additional component, other than deionized (DI) water (e.g., a humectant, an emollient, or a fragrance), may be present in an amount ranging from greater than 0 to about 30 wt % based on a total weight of a given composition.

B. Composition Forms

The compositions of the present invention may have one or more of the following forms.

1. Suspensions

The compositions of the present invention are typically formulated as a suspension having a viscous liquid matrix (e.g., the fluid phase) and particulate material suspended within the viscous liquid matrix.

2. Films or Coatings

The compositions of the present invention may also be present as a film or coating on a substrate, such as skin. Typically, following application of a given composition of the present invention onto a substrate (e.g., skin) in film form, at least a portion of the volatile component evaporates from the composition, leaving a film having a construction as shown in FIG. 2.

Figure 2:
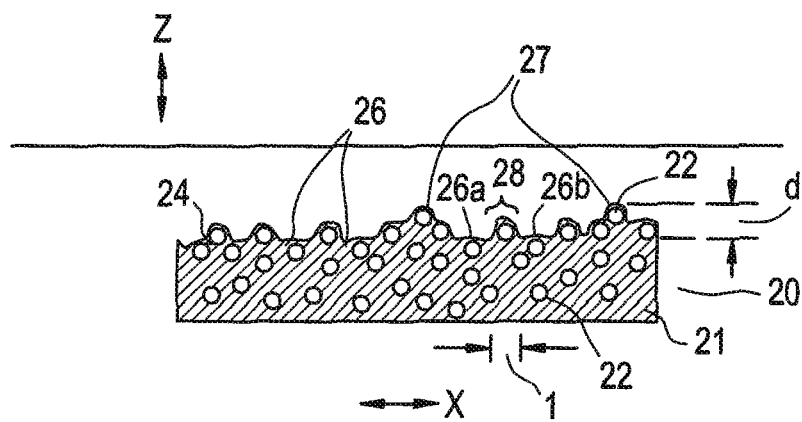
FIG. 2 depicts an exemplary particle loaded film of the present invention.

As shown in FIG. 2, exemplary film 20 comprises a vehicle matrix 21 (e.g., the fluid phase) with particulate material 22 dispersed therein. Exemplary film 20 also has a rough upper surface 24 that results in a substantial amount of light scattering at upper surface 24. Typically, exemplary film 20 exhibits very little, if any, intra-film light scattering given the surface morphology of upper surface 24.

As shown in FIG. 2, upper surface 24 comprises one or more lower surface points 26 along the outermost rough surface (i.e., upper surface 24) and one or more upper surface points 27 along the outermost rough surface (i.e., upper surface 24), wherein one or more lower surface points 26 are separated from one or more upper surface points 27 in a z direction (i.e., a direction normal to the substrate on which exemplary film 20 is placed) by a distance, d, of at least about 0.1 µm, typically from about 0.1 to about 70 µm. Further, portions of upper surface 24 extending between two or more lower surface points 26 may exhibit an arc configuration having an arc angle of greater than about 45° (or greater than about 90', or greater than about 135°), and as much as about 180° or greater. Such upper surface portions, such as upper surface portion 28 shown between lower surface point 26a and lower surface point 26b, exhibit an arc angle of as much as 180° or greater within a distance, l, extending in an x direction between lower surface point 26a and lower surface point 26b. Typically, distance, l, is less than about 20 µm, typically from about 20 to about 1 µm.

In another exemplary embodiment, the composition of the present invention comprises particulate material having a Total Available Fluid Absorption Capacity of Particulate (TAFACP) value of greater than zero; and a fluid phase comprising a non-volatile component, and a volatile component; wherein the particulate material and the non-volatile component possess a substantially similar refractive index. For example, the refractive index of the particulate material and the refractive index of the non-volatile component may we within about 50%, 40%, 30%, 20%, 10%, 9%, 8%, 7%, 6%, 5%, 4%, 3%, 2%, 1%, or may even be identical. In an exemplary embodiment where the particulate material is silica, which has a refractive index of about 1.46, the non-volatile component may have a refractive index ranging from about 1 to about 2, from about 1.25 to about 1.85, from about 1.30 to about 1.80, from about 1.35 to about 1.75, and even 1.40 to about 1.60.

In a further exemplary embodiment, the present invention relates to a transparent coating comprising particulate material having a Total Available Fluid Absorption Capacity of Particulate (TAFACP) value of greater than zero; and a fluid phase comprising a non-volatile component, and a volatile component; wherein the percent diffuse transmission of light to total transmission of light through the transparent coating remains substantially constant as thickness of the coating increases. In this embodiment, the amount of light that is subjected to scattering as it transmits through the coating is limited, thereby allowing the coating to perform effectively no matter how thick the coating may be. This provides a cosmetic product that may be utilized in a number of applications without the need for additional formulation modifications.

In another exemplary embodiment, the present invention relates to a transparent coating for hiding skin imperfections comprising particulate material having a Total Available Fluid Absorption Capacity of Particulate (TAFACP) value of greater than zero; and a fluid phase comprising a non-volatile component, and a volatile component; wherein the particulate material does not provide measurable intra-film light scattering in the coating but provides surface scattering, which hides cutaneous and keratinous imperfections. In this embodiment, light scattering occurs on the surface of the coating and not in the coating, which provides desirable soft focus properties. This effect is further demonstrated by the observation of no measurable light scattering when the coating of this embodiment is over-coated with a polymer that possesses the same or similar refractive index as that of the coating.

Because of the above-described surface morphology of upper surface 24, exemplary film 20 typically exhibits very little intra-film light scattering compared to surface light scattering. In some exemplary embodiments, exemplary film 20 exhibits less than about 50% intra-film light scattering and greater than about 50% surface light scattering based on a total amount of light scattering of exemplary film 20. In other exemplary embodiments, exemplary film 20 exhibits less than about 30% (or less than about 25%, or less than about 20%, or less than about 15%, or less than about 10%, or less than about 5%, or less than about 4%, or less than about 3%, or less than about 2%, or even less than about 1%) intra-film light scattering and greater than about 70% (or greater than about 75%, or greater than about 80%, or greater than about 85%, or greater than about 90%, or greater than about 95%, or greater than about 99%) surface light scattering based on a total amount of light scattering of exemplary film 20.

In addition to having the above-mentioned surface roughness, exemplary film 20 has a desired degree of transparency. Desirably, exemplary film 20 has a desired degree of transparency that enables visual observation of color and tone of a substrate surface (e.g., a skin surface) positioned below exemplary film 20 even when exemplary film 20 has a film thickness of up to about 200 μm. For example, when exemplary film 20 is coated onto skin at a coating thickness of up to about 100 μm, the transparency of exemplary film 20 enables one to visually observe skin color and tone through exemplary film 20. Further, the transparency and composition of exemplary film 20 does not alter the appearance of skin through exemplary film 20 (i.e., skin coated or treated with exemplary film 20 appears substantially identical to untreated skin).

Due to the above-mentioned surface roughness, exemplary film 20 also has a desired degree of obscuring capacity that hides surface imperfections in a substrate surface (e.g., a skin surface) positioned below exemplary film 20 even when exemplary film 20 has a film thickness of as low as about 1 μm. It is believed that the superior obscuration properties of the disclosed films is, at least in part, a result of significant surface light scattering of exemplary film 20 instead of intra-film light scattering.

II. Methods of Making Compositions, Coatings, and Coated Substrates

The present invention is further directed to methods of making compositions suitable for use as cosmetic products such as compositions capable of obscuring surface imperfections. In one exemplary embodiment, the method of making a composition comprises forming a mixture comprising (i) the above-described particulate material having a TAFACP value of greater than zero, and (ii) the above-described fluid phase, wherein the resulting composition has a weight ratio, R, of total non-volatile content (NYC) to TAFACP, ranging from greater than 0 to less than about 8.0.

The methods of making a composition may further comprise one or more additional steps including, but not limited to, incorporating one or more of the above-mentioned additional components into the mixture; mixing the particulate material, the fluid phase and any optional additional components at room temperature; heating the fluid phase (e.g., to a temperature of less than about 100° C.) while adding one or more components to the fluid phase; and packaging the resulting composition in a sealable container (e.g., a sealable jar, a plastic bottle, or a resealable bag).

In another exemplary embodiment, the method of making a composition comprises choosing a particular value of R, wherein R represents a weight ratio of total non-volatile content (NVC) to a TAFACP value of a particulate material; and forming a mixture of (i) the above-described particulate material and (ii) the above-described fluid phase so that a resulting R value of the mixture equals the chosen value of R.

In one desired embodiment, the method of making a composition comprises forming a cosmetic composition specifically formulated for application onto the skin of a human. In this exemplary embodiment, the method typically comprises forming a mixture comprising (i) the above-described particulate material having a TAFACP value of greater than zero, (ii) the above-described fluid phase, wherein the resulting composition has a weight ratio, R, of total non-volatile content (NVC) to TAFACP, ranging from greater than 0 to less than about 8.0, (iii) deionized water, (iv) and, optionally, other cosmetic formulation additives (e.g., humectants, emollients, fragrances, soluble polymers, solidified polymers, or any combination thereof).

The present invention is also directed to methods of forming a coating and methods of forming coated substrates and multi-layer articles. In one exemplary embodiment, a method of forming a coating is disclosed, wherein the method comprises applying any of the above-described compositions onto a substrate. The resulting coated substrate comprises a substrate that is at least partially coated with a suspension or film as described above. The method of forming a coating may further comprise one or more steps including, but not limited to, priming (e.g., washing) the substrate prior to applying the composition.

The methods of forming a coated substrate or multi-layer article may further comprise one or more additional process steps. Suitable additional process steps include, but are not limited to, removing a spreadable/coatable composition from a container, spreading the composition onto the substrate so as to form a film of composition having a desirable film thickness of less than about 200 μm, and repeating any of the above-mentioned steps.

III. Applications/Uses

As discussed above, the compositions of the present invention may be utilized to form coatings on a substrate. Suitable substrates include those where substrate surface defects or imperfections are desirably concealed but still require observation of the substrate surface color and tone. Such substrates include, but are not limited to, cutaneous substrates (e.g., skin), keratinous substrates (e.g., hair, nails, etc.), and even inanimate substrates. In one exemplary embodiment, the compositions of the present invention are used to form a cosmetic treatment over the skin of a human so as to obscure skin imperfections, while showing the natural skin color and tone through the resulting cosmetic treatment. The compositions may be used for daily skin treatment.

EXAMPLES

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Test Methods

The following test methods were used in the examples below.

Determination of Non-Volatile Content

For a given fluid, the fluid was weighed, and then heating at 60° C. for 1 hour. Percent of non-volatile content (% NVC) was calculated using the formula:

% $NVC=((W_o-W_f)\times 100)/W_o$ wherein $W_o$ represents the original weight of the fluid, and $W_f$ represents the final weight of the fluid after the heating step.

Determination of Glossiness of Coating

A given coating was visually observed at approximately 60° from a normal angle to an upper surface of the coating. As used herein, the term "Rough" equals low reflectivity, while the term "Glossy" equals high reflectivity (i.e., shiny).

Determination of Opacity of Coating

A given coating was visually observed at approximately 0° from a normal angle to an upper surface of the coating. As used herein, the term "Opaque" equals substantial hiding of the skin, while "Transparent" equals skin color/tone is seen essentially unaffected by coating.

Determination of Obscuration of Coating

A given coating was visually observed at approximately 0° from a normal angle to an upper surface of the coating. As used herein, the term "Obscuration" equals poor resolution of underlying skin features (e.g., small wrinkles, dark spots freckles, etc.) compared to uncoated skin.

Determination of Oil Adsorption of Particulate Material

The oil absorption of the pigment was measured by the following procedure and is expressed as grams of dibutyl phthalate (DBP) per one gram of pigment. A quantity of sample is charged into the mixing chamber of the torque rheometer (Brabender Instruments, NJ). DBP is dripped into the mixing chamber at a constant rate while the sample is mixed. The torque rheometer measures the torque required to maintain the mixing chamber blades at a constant RPM. The torque vs. time is plotted by an integrator. There is a sharp increase in torque as the sample approaches the saturation point and coalesces, then a sharp decrease after the saturation point is reached and excess oil accumulates in the mixing head. The end point is the point of maximum torque. The amount of DBP used is determined from the integrator printout.

Example 1

Determination of Non-Volatile Content for Various Fluids

Using the above-described method, the weight percent of non-volatile content (% NVC) was calculated for several fluids. The results are shown in Table 1 below.

TABLE 1

| Fluid | Source | % NVC |
|---|---|---|
| Mineral oil, White Heavy | Mallinckrodt Chemicals (Phillipsburg, NJ) | 100% |
| DOW CORNING ® 245 | Dow Corning Corporation (Midland, MI) | 0% |

TABLE 1-continued

| Fluid | Source | % NVC |
|---|---|---|
| DOW CORNING ® 5329 | Dow Corning Corporation (Midland, MI) | 97% |
| DOW CORNING ® 5200 | Dow Corning Corporation (Midland, MI) | 90% |

Example 2

Performance of Coating Formulations Containing Various Concentrations of Non-Volatile Component The performance of sample formulations shown in Table 2 below was evaluated by applying a small amount of a given coating formulation onto skin, allowing the coating formulation to dry for a drying period of 15 minutes, and then evaluating the resulting coating. The appearance of the treated skin area was evaluated in terms of (i) glossiness, (ii) opacity, and (iii) obscuration using the above-described test methods.

Silica gel is prepared according to the process disclosed in U.S. Pat. No. 6,380,265 by mixing an aqueous solution of an alkali metal silicate (e.g., sodium silicate) with a strong acid such as nitric or sulfuric acid, the mixing being done under suitable conditions of agitation to form a clear silica sol which sets into a hydrogel, i.e., macrogel, in less than about one-half hour. The resulting gel is then washed. The concentration of inorganic oxide, i.e., $SiO_2$, formed in the hydrogel is usually in the range of about 10 and about 50 weight percent, with the pH of that gel being from about 1 to about 9, preferably 1 to about 4. A wide range of mixing temperatures can be employed, this range being typically from about 20 to about 50° C. The newly formed hydrogels are washed simply by immersion in a continuously moving stream of water which leaches out the undesirable salts, leaving about 99.5 weight percent or more pure inorganic oxide behind. The pH, temperature, and duration of the wash water will influence the physical properties of the silica, such as surface area (SA) and pore volume (PV). Silica gel washed at 65-90° C. at pH's of 8-9 for 15-36 hours will usually have SA's of 250-400 and form aerogels with PV's of 1.4 to 1.7 cc/gm. Silica gel washed at pH's of 3-5 at 50-65° C. for 15-25 hours will have SA's of 700-850 and form aerogels with PV's of 0.6-1.3. The silica gel, having an oil absorption capacity of 0.8 g oil/1.0 g of silica, is dispersed in a mixture of a volatile component (DOW CORNING® 245 Fluid) and a non-volatile component (mineral oil under the trade name White Heavy, available from Mallinckrodt Chemicals). The total concentration of silica in the mixture remained the same. The concentration of the non-volatile component (NYC) was varied in order to determine the effect of NYC on performance.

The Total Available Fluid Absorption Capacity of Particulate (TAFACP) was calculated from the amount of silica used and its oil absorption capacity. The ratio of NVC/TAFACP was also determined for each sample formulation.

TABLE 2

Sample Coating Formulations

| Composition Component | Sample 1 | Sample 2 | Sample 3 | Sample 4 | Sample 5 | Sample 6 | Sample 7 | Sample 8 | Sample 9 |
|---|---|---|---|---|---|---|---|---|---|
| Silica Gel (g) | 0.5 | 0.5 | 0.5 | 0.5 | 0.5 | 0.5 | 0.5 | 0.5 | 0.5 |
| Mineral Oil, White Heavy (g) | 0 | 0.2 | 0.4 | 0.8 | 1.6 | 2.0 | 2.4 | 2.8 | 3.2 |
| DOW CORNING ® 245 Fluid (g) | 12.5 | 12.3 | 12.1 | 11.7 | 10.9 | 10.5 | 10.1 | 9.7 | 9.3 |
| % Silica Solids | 3.8 | 3.8 | 3.8 | 3.8 | 3.8 | 3.8 | 3.8 | 3.8 | 3.8 |
| TAFACP (g) | 0.4 | 0.4 | 0.4 | 0.4 | 0.4 | 0.4 | 0.4 | 0.4 | 0.4 |
| % Mineral Oil in Fluid Phase | 0 | 1.6 | 3.2 | 6.4 | 12.8 | 16.0 | 19.2 | 22.4 | 25.6 |
| Ratio of total NVC/TAFACP | 0 | 0.5 | 1 | 2 | 4 | 5 | 6 | 7 | 8 |
| Observation at 15 Minutes After Application on Skin | | | | | | | | | |
| Glossiness | Rough | Rough | Rough | Rough | Rough | Rough | Glossy | Glossy | Glossy |
| Opacity | Opaque | Transparent | Transparent | Transparent | Transparent | Transparent | Transparent | Transparent | Transparent |
| Obscuration | Yes | Yes | Yes | Yes | Yes | Yes | None | None | None |

As shown in Table 2, Sample 1 contained no NVC added. The absence of any NVC in Sample 1 resulted in a film, which was rough, but undesirably opaque.

Samples 2-6 provided sample formulations with an increasing amount of NVC, which resulted in an increased ratio value of NVC/Total Available Fluid Absorption Capacity of Particulate (TAFACP) with values ranging from 0.5 to 5. With a ratio value of NVC/TAFACP in this range, the resulting films exhibited all of the desirable characteristics of a cosmetic cream after 15 minutes, namely, a rough, transparent appearance that obscured the underlying skin features.

Samples 7-9 describe provided sample formulations with an increasing amount of NVC, which resulted in an increased ratio value of NVC/Total Available Fluid Absorption Capacity of Particulate (TAFACP) with values ranging from 6-8. With a ratio value of NVC/TAFACP in this range, the resulting films exhibited undesirable glossiness after 15 minutes.

Example 3

Performance of Coating Formulations Containing Various Concentrations of Non-Volatile Component The performance of sample formulations shown in Table 3 below was evaluated by applying a small amount of a given coating formulation onto skin, allowing the coating formulation to dry for a drying period of 15 minutes, and then evaluating the resulting coating. The appearance of the treated skin area was evaluated in terms of (i) glossiness, (ii) opacity, and (iii) obscuration using the above-described test methods.

Silica from Example 1, having an oil absorption capacity of 0.8 g oil/1.0 g of silica, is dispersed in 72.5 g of deionized (DI) water using a homogenizer. Then, a fluid phase was added to the DI water/silica mixture and homogenized for 2-3 minutes, followed by the addition of SEPIGEL™ 305 (commercially available from Southern Soapers (Hampton, Va.)).

Each fluid phase was prepared by mixing one or more of; DOW CORNING® 245 Fluid, mineral oil (White Heavy), DOW CORNING® 5329 and DOW CORNING® 5200. The total concentration of silica each mixture remained the same. The weight of the fluid phase remained constant, but the concentration of non-volatile component (NVC) was varied in order to determine the effect of NVC on performance.

The content of NVC in each sample is shown in Table 3 below. The Total Available Fluid Absorption Capacity of Particulate (TAFACP) was calculated for each sample from the amount of silica used and its oil absorption capacity. The ratio of NVC/Total Available Fluid Absorption Capacity of Particulate (TAFACP) was also determined for each sample, and is shown in Table 3 below.

TABLE 3

Sample Coating Formulations

| Composition Component | Sample 10 | Sample 11 | Sample 12 | Sample 13 | Sample 14 | Sample 15 | Sample 16 | Sample 17 |
|---|---|---|---|---|---|---|---|---|
| DOW CORNING ® 245 Fluid | 32 | 28.8 | 25.6 | 22.4 | 19.2 | 16 | 9.6 | 0 |
| Mineral Oil, White Heavy | 0 | 3.2 | 6.4 | 9.6 | 12.8 | 16 | 22.4 | 32 |
| DOW CORNING ® 5329 | 4 | 4 | 4 | 4 | 4 | 4 | 4 | 4 |
| Silica | 4 | 4 | 4 | 4 | 4 | 4 | 4 | 4 |
| DOW CORNING ® 5200 Formulation Aid | 0.5 | 0.5 | 0.5 | 0.5 | 0.5 | 0.5 | 0.5 | 0.5 |
| Deionized Water | 72.5 | 72.5 | 72.5 | 72.5 | 72.5 | 72.5 | 72.5 | 72.5 |
| SEPIGEL ™305 | 0.6 | 0.6 | 0.6 | 0.6 | 0.6 | 0.6 | 0.6 | 0.6 |

TABLE 3-continued

Sample Coating Formulations

| Composition Component | Sample 10 | Sample 11 | Sample 12 | Sample 13 | Sample 14 | Sample 15 | Sample 16 | Sample 17 |
|---|---|---|---|---|---|---|---|---|
| TAFACP (g) | 3.2 | 3.2 | 3.2 | 3.2 | 3.2 | 3.2 | 3.2 | 3.2 |
| Non-volatile (NVC) Component (g) | 4.7 | 7.9 | 11.1 | 14.3 | 17.5 | 20.7 | 27.1 | 36.7 |
| Ratio of total NVC/TAFACP | 1.5 | 2.5 | 3.5 | 4.5 | 5.5 | 6.5 | 8.5 | 11.5 |
| Observation at 15 Minutes After Application on Skin | | | | | | | | |
| Glossiness | Rough | Rough | Rough | Rough | Rough | Rough | Glossy | Glossy |
| Opacity | Opaque | Opaque | Transparent | Transparent | Transparent | Transparent | Transparent | Transparent |
| Obscuration | Yes | Yes | Yes | Yes | Yes | Yes | None | None |

Samples 10-11 provided sample formulations with an increasing amount of NVC, which resulted in an increased ratio value of NVC/Total Available Fluid Absorption Capacity of Particulate (TAFACP) with values ranging from 1.5 to 2.5. With a ratio value of NVC/TAFACP in this range, the resulting films rough and undesirably opaque.

Samples 12-15 provided sample formulations with an increasing amount of NVC, which resulted in an increased ratio value of NVC/Total Available Fluid Absorption Capacity of Particulate (TAFACP) with values ranging from 3.5-6.5. With a ratio value of NVC/TAFACP in this range, the resulting films exhibited all of the desirable characteristics of a cosmetic cream after 15 minutes, namely, a rough, transparent appearance that obscured the underlying skin features.

Samples 16-17 provided sample formulations with an increasing amount of NVC, which resulted in an increased ratio value of NVC/Total Available Fluid Absorption Capacity of Particulate (TAFACP) with values ranging from 8.5-11.5. With a ratio value of NVC/TAFACP in this range, the resulting films exhibited undesirable glossiness after 15 minutes.

Example 4

Optical Properties of Resulting Film as Film Thickness Increases

The optical properties of the two films (i.e., silica and titania) were evaluated to determine the effect of film thickness on the optical properties of the two films. Films were prepared by forming a composition comprising (i) 23 wt % particles (i.e., $TiO_2$ particles from Sigma-Aldrich or silica gel particles) and (ii) 77 wt % of a polyvinyl alcohol (PVOH) binder material having a refractive index (RI) of about 1.49 to 1.53. The resulting composition had a solids content of 15 wt %. The compositions were spread onto a glass slide with wet film thicknesses ranging from 12 to 100 μm and subsequently dried in a stream of warm air. The resulting films were evaluated at 550 nm using a Shimadzu UV-2401PC UV-VIS spectrophotometer equipped with an Integrating Sphere. The % diffuse transmission to total transmission is calculated by using the formula: 100× (diffuse transmission/total transmission).

As shown in Table 4 below, films containing $TiO_2$ particles (anatase, RI=2.5) exhibited substantial intra-film scattering resulting from the relatively large difference between the refractive index (RI) of the particle and the refractive index (RI) of the PVOH binder material. As the film thickness increased, the film composition exhibited a significant decrease in total transmission (and associated increase in opacity).

In contrast, films containing silica gel particles (RI=1.46) exhibited (i) minimal intra-film scattering resulting from the relatively small difference between the refractive index (RI) of the particle and the refractive index (RI) of the PVOH binder material, and (ii) significant scattering at the film surface as indicated in the % diffuse transmission to total values due to the outermost film surface roughness. The silica gel-containing films had desirable properties of minimal variation with film thickness for both total transmission and % diffuse transmission to total values. Such products desirably provide a very uniform appearance both in obscuration and reflectance to skin even if the film application thickness is not particularly uniform.

TABLE 4

Sample Films

| Particle Type | Total Transmission % | Diffuse Transmission % | % Diffuse Transmission to Total | Film Thickness Wet microns |
|---|---|---|---|---|
| Silica Gel RI = 1.46 | 77.2 | 55 | 71 | 24 |
| | 80.9 | 56.9 | 70 | 40 |
| | 80.6 | 57 | 71 | 50 |
| | 79.9 | 56.9 | 71 | 60 |
| | 83.3 | 55.8 | 67 | 80 |
| | 89.9 | 59.5 | 66 | 100 |
| $TiO_2$ Anatase RI = 2.5 | 69.6 | 34.8 | 50 | 12 |
| | 57.2 | 42.3 | 74 | 24 |
| | 45.9 | 42.0 | 92 | 40 |
| | 40.6 | 29.2 | 97 | 50 |
| | 32.7 | 32.0 | 98 | 60 |
| | 30.2 | 29.7 | 98 | 80 |
| | 24.6 | 24.2 | 98 | 100 |

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% . . . 50%, 51%, 52% . . . 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims. All publications cited herein are incorporated by reference in their entirety.

What is claimed is:

1. A composition comprising:
   from 1.0 to 10.0 weight percent (wt %) of particulate material consisting of hydrophilic silica gel or hydrophilic precipitated silica, based on a total weight of said composition, said particulate material having a Total Available Fluid Absorption Capacity of Particulate (TAFACP) value of greater than zero, an average particle size ranging from 1 to 35 microns, and a pore volume of at least 0.2 cc/g; and
   from 99.0 to 90.0 wt % of a fluid phase based on a total weight of said composition, said fluid phase comprising:
      at least one non-volatile fluid component with each non-volatile fluid component having a non-volatile fluid component refractive index of from 1.2 to 1.8, said non-volatile fluid component refractive index being equal to or different from said particulate material refractive index by less than 10%; and
      at least one volatile fluid component consisting of one or more silicone fluids, deionized water, and any combination thereof;
   said fluid phase comprising from 1.0 to 40.0 wt % of said at least one non-volatile fluid component, and from 99.0 to 60.0 wt % of said at least one volatile fluid component, based on a total weight of said fluid phase;
   wherein said composition has a weight ratio, R, of total non-volatile content (NVC) to TAFACP, and R ranges from greater than 0 to less than 8.0, and
   wherein the composition forms a transparent film when applied onto a cutaneous or keratinous substrate at a coating thickness of up to 100 μm.

2. The composition of claim 1, wherein said particulate material has an average particle size ranging from 1 to 20 microns.

3. The composition of claim 1, wherein said fluid phase comprises two or more distinct phases.

4. The composition of claim 1, wherein R ranges from 0.5 to 7.4.

5. The composition of claim 4, wherein R ranges from 2.0 to 6.0.

6. The composition of claim 4, wherein said composition further comprises one or more additional components selected from surfactants, fragrances, soluble polymers, or any combination thereof.

7. A composition for forming a transparent coating having a desired degree of obscuration, said composition comprising:
   particulate material consisting of hydrophilic silica that has not been surface treated to alter surface properties of the silica, said hydrophilic silica having a Total Available Fluid Absorption Capacity of Particulate (TAFACP) value of greater than zero, an average particle size ranging from 1 to 35 microns, and a pore volume of at least 0.2 cc/g; and
   a fluid phase comprising:
      at least one non-volatile fluid component with each non-volatile fluid component having a non-volatile fluid component refractive index of from 1.2 to 1.8, said non-volatile fluid component refractive index being equal to or different from a particulate material refractive index of said hydrophilic silica by less than 10%;
      at least one volatile fluid component comprising one or more components selected from volatile silicone fluids, deionized water, and any combination thereof; and
      optionally one or more fluid phase additives selected from humectants, surfactants, emollients, fragrances, soluble polymers, or any combination thereof;
   wherein said composition has a weight ratio, R, of total non-volatile content (NVC) to TAFACP, and R ranges from greater than 0 to less than 8.0; and
   wherein the composition forms a transparent film when applied onto a cutaneous or keratinous substrate at a coating thickness of up to 100 μm.

8. The composition of claim 7, wherein said at least one non-volatile fluid component consists of one or more components selected from non-volatile silicone fluids, oils, waxes, glycerin, and any combination thereof.

9. The composition of claim 7, wherein said fluid phase consists of (i) said at least one non-volatile fluid component; (ii) said at least one volatile fluid component; and (iii) one or more fluid phase additives selected from humectants, surfactants, emollients, fragrances, soluble polymers, or any combination thereof.

10. The composition of claim 7, wherein said at least one non-volatile fluid component consists of mineral oil, one or more non-volatile silicone fluids, or a combination thereof; and said at least one volatile fluid component consists of one or more volatile silicone fluids.

11. A composition for forming a transparent coating having a desired degree of obscuration, said composition consisting of:
   particulate material consisting of hydrophilic silica, that has not been surface treated to alter surface properties of the silica, said particulate material having a Total Available Fluid Absorption Capacity of Particulate (TAFACP) value of greater than zero, an average particle size ranging from 1 to 35 microns, and a pore volume of at least 0.2 cc/g; and
   a fluid phase consisting of:
      at least one non-volatile fluid component with each non-volatile fluid component having a non-volatile fluid component refractive index of from 1.2 to 1.8, said non-volatile fluid component refractive index being equal to or different from said particulate material refractive index by less than 10%;
      at least one volatile fluid component consisting of one or more volatile silicone fluids, deionized water, or a combination thereof; and
      optionally one or more fluid phase additives selected from ethanol, humectants, surfactants, emollients, fragrances, soluble polymers, or any combination thereof;
   wherein said composition has a weight ratio, R, of total non-volatile content (NVC) to TAFACP, and R ranges from greater than 0 to less than 8.0; and wherein the composition forms a transparent film when applied onto a cutaneous or keratinous substrate at a coating thickness of up to 100 µm.

12. The composition of claim 1, wherein said non-volatile fluid component refractive index is equal to said particulate material refractive index.

13. The composition of claim 1, wherein said non-volatile fluid component refractive index is from 1.4 to 1.6.

14. The composition of claim 11, wherein said hydrophilic silica has an average particle size ranging from 1 to 20 microns, said hydrophilic silica being present in an amount ranging from 2 wt % to 8 wt % based on a total weight of the composition.

15. The composition of claim 1, wherein said fluid phase consists of: (a) at least one non-volatile fluid component consisting of mineral oil, a wax, one or more non-volatile silicone fluids, or a combination thereof, (b) at least one volatile fluid component consisting of one or more volatile silicone fluids, deionized water, and any combination thereof, and (c) fluid phase additives comprising a surfactant and a soluble polymer.

16. The composition of claim 7, wherein said particulate material is present in an amount ranging from 1.0 to 10.0 wt %, and said fluid phase is present in an amount ranging from 99.0 to 90.0 wt %, based on a total weight of said composition.

17. The composition of claim 11, wherein said particulate material is present in an amount ranging from 1.0 to 10.0 wt %, and said fluid phase is present in an amount ranging from 99.0 to 90.0 wt %, based on a total weight of said composition.

18. The composition of claim 1, wherein said at least one non-volatile fluid component consists of one or more components selected from non-volatile silicone fluids, oils, waxes, glycerin, and any combination thereof.

19. The composition of claim 7, wherein said at least one non-volatile fluid component consists of one or more components selected from non-volatile silicone fluids, oils, waxes, glycerin, and any combination thereof.

20. The composition of claim 7, wherein said hydrophilic silica consists of silica gel or precipitated silica.

* * * * *